(12) United States Patent
Mueller

(10) Patent No.: US 9,797,853 B2
(45) Date of Patent: Oct. 24, 2017

(54) INSULATION RESISTANCE MEASUREMENT FOR INVERTERS

(71) Applicant: SMA Solar Technology AG, Niestetal (DE)

(72) Inventor: Burkard Mueller, Kassel (DE)

(73) Assignee: SMA Solar Technology AG, Niestetal (DE)

( * ) Notice: Subject to any disclaimer, the term of this patent is extended or adjusted under 35 U.S.C. 154(b) by 402 days.

(21) Appl. No.: 14/556,290

(22) Filed: Dec. 1, 2014

(65) Prior Publication Data

US 2015/0084654 A1    Mar. 26, 2015

Related U.S. Application Data

(63) Continuation of application No. PCT/EP2013/061019, filed on May 29, 2013.

(30) Foreign Application Priority Data

Jun. 1, 2012  (DE) .................. 10 2012 104 752

(51) Int. Cl.
*G01R 31/02* (2006.01)
*G01N 27/04* (2006.01)
(Continued)

(52) U.S. Cl.
CPC ........... *G01N 27/04* (2013.01); *G01R 27/025* (2013.01); *G01R 27/16* (2013.01); *G01R 31/42* (2013.01); *G01R 31/025* (2013.01)

(58) Field of Classification Search
USPC ................. 324/541, 544, 551, 557
See application file for complete search history.

(56) References Cited

U.S. PATENT DOCUMENTS 5,712,572 A * 1/1998 Tamechika .............. H02S 50/10
                                                    324/509
6,320,769 B2    11/2001 Kurokami et al.
(Continued)

FOREIGN PATENT DOCUMENTS

CN          102298091 A      12/2011
DE       102006031663 B3     11/2007
(Continued)

OTHER PUBLICATIONS

International Search Report dated Sep. 19, 2013 for International application No. PCT/EP2013/061019.

*Primary Examiner* — Vincent Q Nguyen
(74) *Attorney, Agent, or Firm* — Eschweiler & Potashnik, LLC

(57) ABSTRACT

During measuring an insulation resistance for an inverter having at least one half-bridge including two active switching elements for driving an output current, and a DC link voltage, a center point of the half-bridge positioned between the switching elements is connected to a grounding point by closing a grounding switch, and the center point connected to the grounding point is connected, one after the other, to a first ungrounded terminal and a second ungrounded terminal of the DC link voltage of the inverter present at the half-bridge by means of the two active switching elements of the half-bridge to establish a connection between the first and second ungrounded terminals, respectively, and the grounding point. A current flowing via the connection to the grounding point is measured using a measuring device.

25 Claims, 4 Drawing Sheets

(51) Int. Cl.
*G01R 31/42* (2006.01)
*G01R 27/02* (2006.01)
*G01R 27/16* (2006.01)

(56) References Cited

U.S. PATENT DOCUMENTS

| | | |
|---|---|---|
| 7,576,547 B2 | 8/2009 | Mueller |
| 8,521,673 B2 | 8/2013 | Todorokihara |
| 9,124,183 B2 | 9/2015 | Oldenkamp |
| 2007/0195578 A1 | 8/2007 | Murakuki et al. |
| 2008/0007277 A1 | 1/2008 | Backhaus |
| 2009/0134881 A1* | 5/2009 | Tachizaki .............. B60L 3/0023 324/551 |
| 2012/0026631 A1 | 2/2012 | Kazemi et al. |
| 2012/0119755 A1* | 5/2012 | Ishii ..................... G01R 27/025 324/551 |
| 2012/0163048 A1* | 6/2012 | Victor ..................... H02H 3/16 363/55 |

FOREIGN PATENT DOCUMENTS

| | | |
|---|---|---|
| DE | 102010054413 A1 | 8/2011 |
| DE | 102011007222 A1 | 10/2012 |
| EP | 1143594 A2 | 10/2001 |
| EP | 1857825 A1 | 11/2007 |
| JP | H01165973 A | 6/1989 |
| JP | H0694762 A | 4/1994 |
| JP | H11122819 A1 | 4/1999 |
| JP | 2006238573 A | 9/2006 |
| WO | 2012140149 A2 | 10/2012 |

* cited by examiner

INSULATION RESISTANCE MEASUREMENT FOR INVERTERS

REFERENCE TO RELATED APPLICATIONS

This application is a continuation of International application number PCT/EP2013/061019, filed on May 29, 2013, which claims priority to German application number 10 2012 104 752.9, filed on Jun. 1, 2012.

FIELD

This disclosure relates to a method of measuring an insulation resistance for an inverter having at least one half-bridge comprising two active switching elements for driving an output current, and to an inverter comprising at least one half-bridge having two active switching elements and comprising an apparatus for measuring an insulation resistance.

BACKGROUND

EP 1 857 825 A1 and the parallel document U.S. Pat. No. 7,576,547 B2 disclose a measuring arrangement comprising a grounding point for determination of the insulation resistance of a live electrical apparatus or of an installation with a supply voltage with a positive terminal and a negative terminal. In this case, two switches or a corresponding changeover switch are provided, which each produce a current path between one of the two terminals and a grounding point in order to determine the total insulation resistance that results in the event of the occurrence of one or more insulation faults with any arbitrary potential reference. In order to determine the insulation resistance, two successive measurements are performed, wherein, in the first of these measurements, the first switch is closed while the second switch is open, and wherein, in the second of these measurements, the first switch is open while the second switch is closed. During the measurements, the current flowing via the respectively produced connection to the grounding point is measured. The insulation resistance is calculated from the two measured currents, in respect of which the cited documents provide a detailed instruction.

The known measuring arrangement can be provided specifically for monitoring a photovoltaic system that feeds electrical energy from a photovoltaic generator into an AC grid for an insulation fault. The component parts to be provided for forming the known measuring arrangement at an inverter are numerous and increase the total costs of the inverter considerably.

DE 10 2006 031 663 B3 discloses a method for measuring the insulation resistance in an IT network. This IT network has a DC link and a self-commutated converter comprising a first and a second power switch. Furthermore, a measuring arrangement for measuring of the DC link voltage with respect to ground consisting of a voltage divider and two associated potential measuring devices is part of the IT network. The method comprises offline measurement, for example at the beginning of operation, in which all of the first or all of the second power switches of the converter are closed. In this switching state, the two potentials of the DC link and the DC link voltage are measured and the insulation resistance is determined from this.

DE 10 2010 054 413 A1 discloses a method for localizing an insulation fault in a system that has a DC section with a high side and a low side and an AC section including an inverter with a series circuit comprising two power switches that are connected between the high side and the low side. A DC voltage from a DC voltage source is supplied to the DC section. The power switch present directly on the high side is turned on, the power switch present directly on the low side is turned on, in each case a high-side insulation voltage between the high side and a ground and a low-side insulation voltage between the low side and ground are measured in each of the two on states and finally, on the basis of the measurement results, it is determined whether there is an insulation fault in the DC or AC section.

DE 10 2011 007 222 A1, which was not published until after the priority date of the present application, discloses an inverter circuit in which, for insulation monitoring, a voltage divider ratio of a voltage divider used for insulation monitoring is changed by means of AC voltage shunts of the inverter by virtue of said shunts being coupled to DC link potentials by means of IGBTs in a bridge circuit. During normal operation of the inverter, the voltage present at the AC voltage shunts represents the instantaneous value of the output voltage and is used for regulation thereof. The insulation monitoring takes place by virtue of voltage measurement of an actual voltage in the form of a potential difference between a DC link potential and ground. The actual voltage is compared with a preset setpoint voltage that is dependent on the switch position of the IGBTs. An insulation fault is indicated when a difference between the actual voltage and the setpoint voltage exceeds a preset degree.

There still is a need of a method of measuring an insulation resistance for an inverter and an inverter comprising an apparatus for measuring an insulation resistance that use active measurement of the insulation resistance without incurring high costs for this.

SUMMARY

The present disclosure provides a method of measuring an insulation resistance for an inverter having at least one half-bridge comprising two active switching elements for driving an output current, and a DC link voltage. The method comprises connecting a center point of the half-bridge positioned between the switching elements to a grounding point by closing a grounding switch, and connecting the center point connected to the grounding point, one after the other, to a first ungrounded terminal and a second ungrounded terminal of the DC link voltage of the inverter present at the half-bridge by means of the two active switching elements of the half-bridge to establish a connection between the first and second ungrounded terminals, respectively, and the grounding point. The method further comprises measuring a current flowing via the connection to the grounding point using a measuring device.

The present disclosure further provides an inverter comprising a first ungrounded terminal and a second ungrounded terminal, between which a DC link voltage is present in operation of the inverter; at least one half-bridge connected between the first and second ungrounded terminals; and an apparatus for measuring an insulation resistance. The at least one half-bridge has two active switching elements for driving an output current and a center point positioned between the two active switching elements. The apparatus comprises a grounding switch configured to connect the center point of the half-bridge to a grounding point. The apparatus is configured to connect the center point connected to the grounding point, one after the other, to the first and second ungrounded terminals by means of the two active switching elements of the half-bridge, respectively, to establish a connection between the first and second ungrounded terminals and the grounding point; and the apparatus is configured to measure a current flowing via the connection to the grounding point using a measuring device.

Other features and advantages of the present disclosure will become apparent to one with skill in the art upon examination of the following drawings and the detailed description. It is intended that all such additional features and advantages be included herein within the scope of the present disclosure, as defined by the claims.

BRIEF DESCRIPTION OF THE DRAWINGS

The present disclosure can be better understood with reference to the following drawings. The components in the drawings are not necessarily to scale, emphasis instead being placed upon clearly illustrating the principles of the present disclosure. In the drawings, like reference numerals designate corresponding parts throughout the several views.

DETAILED DESCRIPTION

Figure 1:
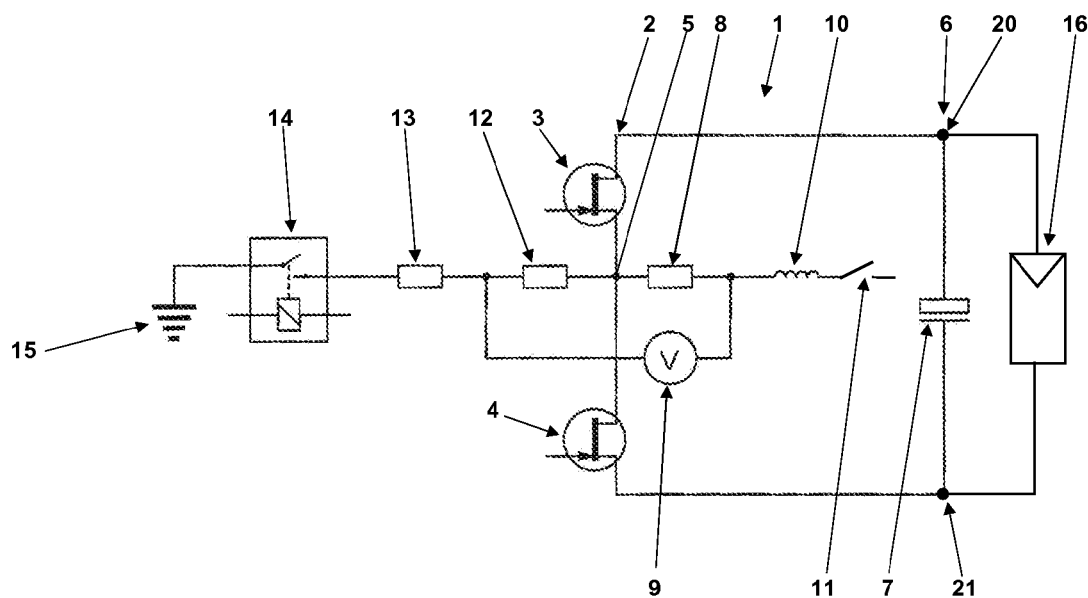
FIG. 1 illustrates a first embodiment of relevant details of an inverter according to the present disclosure comprising an apparatus for measuring an insulation resistance.

This disclosure relates to a method of measuring an insulation resistance for an inverter having at least one half-bridge comprising two active switching elements for driving an output current, and to an inverter comprising at least one half-bridge having two active switching elements and comprising an apparatus for measuring an insulation resistance.

The inverter can be, for example, a photovoltaic (PV) inverter, i.e. can feed electrical energy from a photovoltaic generator into an AC grid.

The inverter can have an output-side transformer. However, it can also in particular be a transformerless inverter.

The measured insulation resistance does include that of the inverter itself, but it is in particular the insulation resistance of a current source connected on the input side to the inverter, i.e. of a PV generator, for example.

During operation of the inverter, the current source can have a reference to ground. Thus, for example, one of its terminals can be grounded during operation of the inverter. Even during operation of a transformerless inverter on a grounded grid, a reference to ground of an otherwise ungrounded current source is produced via the line voltage present at the outputs of the inverter. For the measurement of the insulation resistance, such connections to ground need to be eliminated, however, since the insulation resistance is measured with respect to ground.

When implementing the principle of active measurement of the insulation resistance for an inverter according to the present disclosure, a center point positioned between the two active switching elements of a half-bridge of the inverter is connected to a grounding point by closing a grounding switch. The center point connected to the grounding point is then connected to the two ungrounded terminals of a DC link voltage of the inverter that is present at the half-bridge one after the other by means of the switching elements of the half-bridge, which are used for driving an output current during normal operation of the inverter. The current flowing via the connection to the grounding point produced in this way is measured. The measured values are then evaluated in a manner known in principle.

When no DC-to-DC converters are used on the input side, the DC link voltage that is present at the half-bridge of the inverter and whose terminals are alternately connected to the grounding point is equal to an input voltage of the inverter, which is provided by the connected current source.

If, in the definition of the present disclosure, reference is made to a current flowing to the grounding point, it is not a specific direction of current flow that is being referred to thereby. Rather, the direction of current flow is dependent on the polarity of the voltage with respect to ground that drives this current. Since the two terminals of the DC link voltage of the inverter normally have different polarities with respect to ground, the direction of current flow changes at least when the center point of the half-bridge is first connected for a longer period of time to one terminal of the DC link voltage and then for a longer period of time to the other terminal of the DC link voltage.

The method according to the present disclosure makes use of the active switching elements of a half-bridge of the inverter for the production of the connection of the two ungrounded terminals of the DC link voltage of the inverter to the grounding point. That is to say that switching elements that are present in any case in the inverter and to which corresponding voltages can be applied are used as switches for connecting the two terminals of the DC link voltage. Already by this means can the costs of the measurement of the insulation resistance at an inverter be markedly reduced in comparison with a separate measuring arrangement as known from EP 1 857 825 A1 and the parallel document U.S. Pat. No. 7,576,547 B2. The connection to be produced between the center point of the half-bridge and the grounding point for the measurement of the insulation resistance in contrast does not require a switch that can be subjected to greater loading, in particular when a protective resistor with a higher resistance is provided in this connection.

In the method according to the present disclosure for measuring the insulation resistance, not only are the switching elements of the half-bridge of the inverter actuated in a manner that is unconventional in comparison with the normal operation of the inverter during feeding into a connected AC grid, but the inverter is also not yet connected to the AC grid at the time of measurement or it is disconnected from the AC grid, which is connected during its normal operation, again for the measurement of the insulation resistance.

In one embodiment, the current flowing via the connection to the grounding point is measured as a voltage drop across a shunt that is connected between the center point of the half-bridge and the grounding point. This includes that the connection of the two terminals of the DC link voltage to the grounding point leads via the same shunt and that, correspondingly, also only one measuring device is required.

This measuring device may be such a measuring device of the inverter that measures a voltage drop across a shunt that has a lower resistance than the shunt between the center point of the half-bridge and the grounding point during normal operation of the inverter in order to measure a current from the half-bridge into the connected AC grid.

That is to say that, in the method according to the present disclosure, use can be made of devices that are provided in any case in the inverter, even in respect of the measuring device for the current flowing to the grounding point, which further reduces the additional costs for the implementation of the measurement method according to the present disclosure.

Specifically, in the measurement method according to one embodiment of the present disclosure, the switching elements can be closed one after the other and in each case only once during the measurement in order to allow two direct currents to flow, one after the other, from the two terminals of the DC link voltage via the connection to the grounding point. This corresponds to an implementation of the measurement principle known from EP 1 857 825 A1 and U.S. Pat. No. 7,576,547 B2. However, this implementation presupposes that the switching elements of the half-bridge can be closed for a considerably longer time, i.e. a time that is longer by a multiple, than is necessary during normal inverter operation. Even when the loads on the switching elements occurring in the process, in particular when a protective resistor is arranged in the connection to the grounding point, are only low, prolonged closing may nevertheless be impossible because, for example, the drivers of the switching elements are supplied with voltage by means of a bootstrap circuit.

Even in this case, however, an embodiment of the method according to the present disclosure can be applied in which the switching elements are actuated in order to allow a periodic alternating current to flow via the connection through a line choke of the inverter to the grounding point or in order to set up at least a driving voltage for the current to the grounding point at the center point of the half-bridge that lies between the voltages of the two terminals of the DC link voltage with respect to ground. That is to say that the switching elements can be actuated, for example, in accordance with the principle of pulse width modulation in such a way that an alternating current is driven into the grounding point via a filter comprising a line choke and eventually further elements such as a filter capacitor and a protective resistor. This alternating current may not only be sinusoidal, but also square-wave, for example, and has a very low frequency in order that it allows a meaningful measurement of the insulation resistance even in the case of relatively high leakage capacitances of a current source connected to the inverter. Specifically, the period of the alternating current formed for measuring the insulation resistance can have a period that is longer than that of an alternating current output by the line choke during normal operation of the inverter by at least a factor of 2, preferably by at least a factor of 5, further preferably still by at least a factor of 10, further preferably still by at least a factor of 50 and most preferably by at least a factor of 100. In other words, the period of the alternating current for the measurement of the insulation resistance can quite easily be one or more and even a few tens of seconds. The ideal period length for sufficiently precise measurement of the insulation resistance is dependent in this case on the time constant from the available leakage capacitances and the insulation resistance itself, wherein the latter can vary significantly, for example as a result of climatic conditions in the case of a photovoltaic generator connected to the inverter. The insulation resistance sought can be calculated from the low-frequency alternating current when the AC voltage driving said current is detected at the same time. This can take place using a measuring device that measures the AC voltage when it forms as a voltage drop across a filter capacitor, for example.

When the voltage driving the current to the grounding point relative to one of the terminals of the DC link voltage is detected or it can be assumed to be known owing to defined actuation of the switching elements of the half-bridge, a voltage forming as a voltage drop between a point positioned between the already mentioned protective resistor for the grounding switch and the grounding point and the one of the terminals of the DC link voltage can also be measured in order to measure the current flowing via the connection to the grounding point. This applies irrespective of whether the driving voltage is an AC voltage or an at least temporarily constant voltage, such as, for example, a voltage between the voltages of the two terminals of the DC link voltage with respect to ground. On the basis of Kirchhoff's voltage law, the sum of the voltage between this point and the one of the terminals of the DC link voltage, on the one hand, and the driving voltage relative to this one of the terminals, on the other hand, is equal to the voltage drop across the protective resistor. The current flowing to the grounding point can be calculated from the voltage drop across the protective resistor. In the method according to the present disclosure, the voltages that are detected for detecting the currents flowing to the grounding point can, however, also be used directly, i.e. without any explicit conversion into current intensities, as a measure of the currents for calculating the insulation resistance of interest.

When the point at which the voltage with respect to the one of the terminals of the DC link voltage is measured in order to measure the current flowing via the connection to the grounding point is between the protective resistor and the grounding switch, the voltage measurement at this point can be performed even during normal operation of the inverter, i.e. when the grounding switch is open, and can be used to detect the voltage at the output of the filter, for example.

When mention is made in this description of an alternating current to the grounding point and an AC voltage driving said alternating current, this does not mean that the current flowing to the grounding point needs to change its direction of current flow and that the voltage driving said current with respect to ground needs to change its polarity correspondingly. The actuation of the switching elements of the half-bridge can also take place, for example, in such a way that the instantaneous value of the driving AC voltage varies by less than half the DC link voltage, and that the AC voltage has a DC voltage offset in the direction of a terminal of the DC link voltage, with the result that the current driven thereby has a fixed direction of current flow.

In order to alternately connect the two terminals of the DC link voltage of the inverter to a grounding point, the apparatus of an inverter according to the present disclosure that is provided for measuring an insulation resistance does not have any additional switches, but instead makes use of the switching elements of a half-bridge of the inverter for this purpose. In addition to the actual inverter circuit of the inverter, however, the apparatus has a grounding switch in order to connect the center point of the half-bridge to the grounding point. This switch is connected in series with a shunt between the center point of the half-bridge and the grounding point in order to measure the current flowing to ground. This shunt is typically connected in series with an additional protective resistor, which limits the current flowing to the grounding point. The shunt can alternatively also be configured as a protective resistor itself. In order to disconnect the center point of the half-bridge from an AC grid connected to the inverter on the output side, the apparatus uses a mains switch, a mains relay or a mains contactor of the inverter.

The voltage drop across the shunt and, thus, the current flowing through said shunt is measured by the apparatus for measuring the insulation resistance, for example, using a measuring device that measures a voltage drop across a shunt with a lower resistance during normal operation of the inverter in order to measure a current driven by the half-bridge into the connected AC grid. In this case, a branch can be provided at or downstream of the center point of the half-bridge, which branch leads on the one hand to the shunt for measuring the insulation resistance and on the other hand to the shunt with the lower resistance and furthermore to the line choke and finally to the mains switch or mains relay or mains contactor. A measuring device that is connected to those connections of the two shunts that are on the other side from the branch does in principle measure the sum of the voltage drops across the two shunts. However, during the measurement of the insulation resistance, there is no voltage drop across the shunt with the lower resistance since the mains switch is open, while there is no voltage drop across the shunt for measuring the insulation resistance during normal operation of the inverter since in this case the grounding switch of the apparatus for measuring the insulation resistance is open. Thus, the measuring device connected in such a way only ever measures the voltage drop of interest in each case.

Alternatively, the apparatus for measuring the insulation resistance can have a changeover switch that conducts the current from the center point of the half-bridge either through the shunt for measuring the insulation resistance or through the shunt with the lower resistance, wherein the measuring device is connected to a branch to the shunts and is connected to that connection of the changeover switch that is on the other side thereof. The side of the resistors on which the changeover switch is provided and the side on which the fixed branch to the shunts is provided is inconsequential in this case. The measuring device in any case detects the voltage drop across the shunt respectively selected by the changeover switch.

Both of the above-described connection possibilities for the measuring device can be applied both when the apparatus closes the switching elements one after the other in order to allow two direct currents to flow, one after the other, via the connection to the grounding point. Both of the above-described connection possibilities for the measuring device can be applied also when the apparatus actuates the switching elements in order to allow an alternating current to flow via the connection through a line choke of the inverter to the grounding point or in order to set other driving voltages, between the voltages of the terminals of the DC link voltage with respect to ground, for the current to the grounding point at the center point of the half-bridge. It goes without saying that, in the second and latter case, the branch to the grounding point in the first connection variant of the measuring device should only be provided downstream of the line choke. In this latter case, it is additionally desirable if a filter capacitor is connected in parallel with the shunt for the measurement of the insulation resistance, which filter capacitor filters out switching ripple, resulting from the switching elements of the half-bridge actuated at high frequency, with respect to the low-frequency alternating current to ground actually of interest. In order to measure the driving AC voltage of the alternating current, the apparatus for measuring the insulation resistance can have an additional measuring device that measures the AC voltage drop across a filter capacitor.

Referring now in greater detail to the drawings, FIG. 1 illustrates an inverter 1 in the form of its parts that are essential here, which include a half-bridge 2 comprising switching elements 3 and 4 on both sides of a center point 5, a DC link circuit 6 comprising a DC link capacitor 7, a shunt 8 comprising an assigned measuring device 9 for the voltage drop across said shunt, a line choke 10 and a mains switch 11. The DC link circuit 6 is in this case connected directly to a current source 16, for example; a connection of the current source 16 to the DC link 6 via a DC-to-DC converter without galvanic isolation, such as, for example, a step-up converter, would also be possible. In addition to the current path from the center point 5, which passes through the shunt 8 and through the line choke 10 to the mains switch 11, via which the inverter can be connected to an AC grid in order to feed into this AC grid, a further current path branches off from the center point 5. This current path leads through a shunt 12 with a higher resistance than the shunt 8, a protective resistor 13 and a grounding switch 14 to the grounding point 15. The shunt 12 is connected in series with the shunt 8 between the connections of the measuring device 9. Both the mains switch and the grounding switch can be embodied as relays or contactors in order to be able to be actuated in automated fashion.

When the grounding switch 14 is closed with the mains switch 11 open, the center point 5 is connected to the grounding point 15 via the resistors 12 and 13. Then, by closing the switching element 3, the positive terminal 20 of a DC link voltage of the DC link circuit 6 can be connected to the center point 5 and, thus, to the grounding point 15 in order to measure a current flowing as a result to the grounding point 15 using the measuring device 9. In the process, the measuring device 9 only measures a voltage drop across the shunt 12 as a measure of the current of interest because there is no current flowing through the shunt 8 owing to the open mains switch 11 and there is therefore no voltage drop across the shunt 8.

When the current to the grounding point 15 is measured, the switching element 3 can be opened again and then the switching element 4 can be closed in order to measure, in the same way, a current flowing from the negative terminal 21 of the DC link voltage of the DC link circuit 7 to the grounding point 15. In a known manner, the insulation resistance of the arrangement shown can be determined from the measured values of the two currents to the grounding point 15. For this purpose, only the shunt 12, the protective resistor 13 and the grounding switch 14 are required as additional component parts over the basic design of the inverter 1. The measured insulation resistance is determined in particular from insulation resistances in the region of a current source 16 connected to the DC voltage link 6, in this case a photovoltaic generator, but also includes the intrinsic insulation resistance of the inverter 1.

Figure 2:
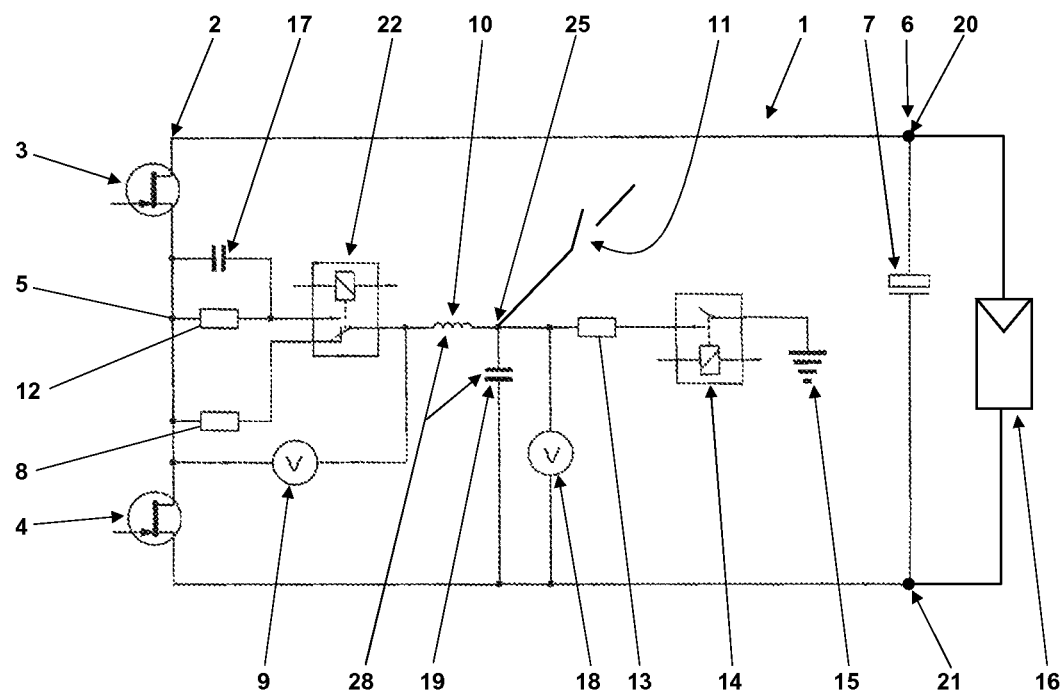
FIG. 2 illustrates the essential component parts of a second embodiment of an inverter according to the present disclosure comprising an apparatus for measuring an insulation resistance.

The inverter 1 illustrated in FIG. 2 by its component parts that are essential to the present disclosure has an additional changeover switch 22 that conducts the current to the line choke 10 either through the shunt 8 with the lower resistance or through the shunt 12 with the higher resistance. In this case, the current path through the protective resistor 13 and the grounding switch 14 to the grounding point 15 branches off from the current path through the mains switch 11 into the electricity grid (again not shown here) into which the inverter 1 feeds only downstream of the line choke 10. With this topology of the inverter 1, the switching elements 3 and 4 can be actuated in such a way that they set a very low-frequency AC voltage component at a filter output 25 of a filter 28 comprising the line choke 10 and a filter capacitor 19, by means of which AC voltage component again a very low-frequency current is driven into the grounding point 15. It goes without saying that, in this case, the mains switch 11 is open and the grounding switch 14 is closed. Furthermore, a filter capacitor 17 is connected in parallel with the shunt 12 in order to filter away the high-frequency component of the current through the choke 10.

The driving voltage of this alternating current is measured by an additional measuring device 18 across the filter capacitor 19. The insulation resistance of the inverter 1 can be determined from the ratio of the alternating current to its driving AC voltage. For this purpose, both of the voltage at the filter capacitor 19 and of the current through the shunt 12, only the low-frequency AC components $U_{AC}$ and $I_{AC}$ need to be evaluated. The insulation resistance $R_{iso}$ then results in accordance with $R_{iso}=U_{AC}/I_{AC}-R_{13}$, where $R_{13}$ is the value of the protective resistor 13. The filter capacitor 19 is in this case of no significance for the measurement of $U_{AC}$ but expediently takes up the high-frequency ripple current of the line choke 10. This corresponds to the ripple during normal feed-in operation of the inverter 1 and is thus a multiple greater than the measured current. If the filter capacitor 19 were to have been omitted, the current in the line choke 10 could change only to a minimal extent, and the protective resistor 13 would have been subjected to the entire high-frequency AC voltage at the center point 5, with the result that its loading would have been very high. Since the filter capacitor 19 is in any case present in a line filter of an inverter 1, however, it can take on the filter function required here. The determination of the insulation resistance from the ratio of the alternating current and its driving AC voltage does not presuppose that the switching elements 3 and 4 can be permanently closed. For this determination, the changeover switch 22 is not absolutely necessary either. Instead, the current paths to the mains switch 11 and the grounding switch 14 could branch to the shunts 8 and 12 only after the line choke 10, wherein the filter capacitor 17 could also then be connected in parallel with the shunt 12, although in this case the filter capacitor 19 would already filter. Often, however, the line choke 10 and the filter capacitor 19 are directly connected to one another, in particular when they are cast as a filter unit with one another and possibly with further components, with the result that an arrangement as shown in the drawings is enforced. The usual location of the shunt 8 for the current driven by the half-bridge 2 in an inverter 1 is therefore between the center point 5 and the choke 10.

The functional principle of the measuring devices 9 and 18 is not critical for the present disclosure. However, it may be advantageous to use delta-sigma converters, which are analog-to-digital converters with a very high resolution, as measuring devices 9 and 18.

In the embodiment of the present disclosure explained with reference to FIG. 2, it is also possible to dispense with the protective resistor 13 because the amplitude of the current can be limited solely by actuation of the switching elements 3 and 4 so as to generate the alternating current to the grounding point 15.

Figure 3:
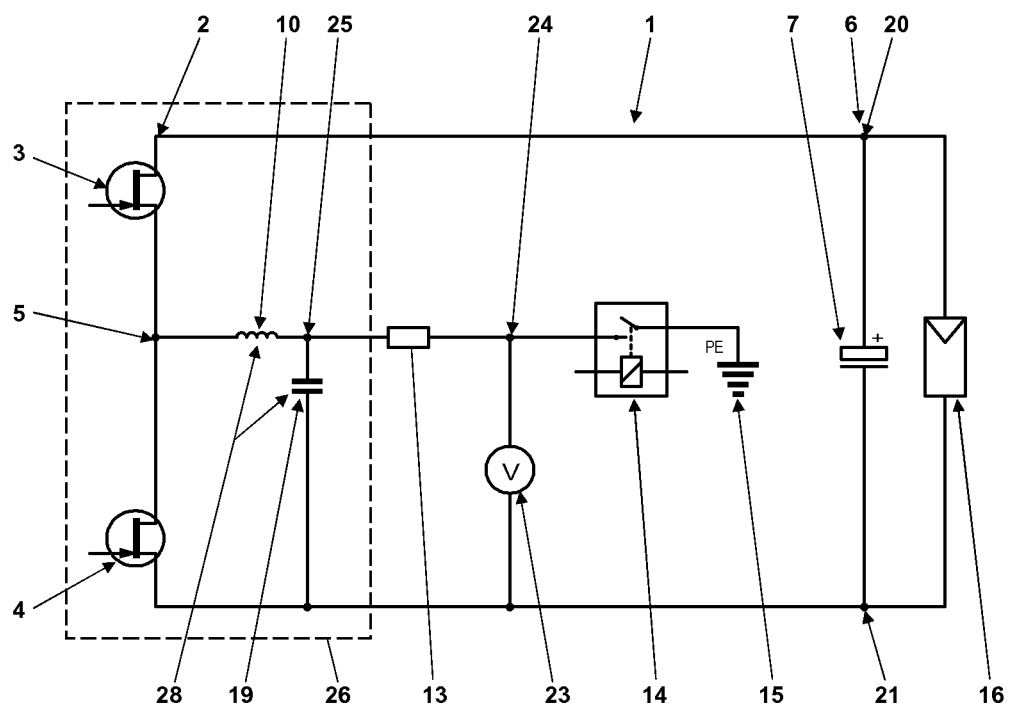
FIG. 3 illustrates the essential component parts of a third embodiment of an inverter according to the present disclosure comprising an apparatus for measuring an insulation resistance.

In the illustration of essential parts of the inverter 1 shown in FIG. 3, the mains switch 11 is not shown, although it is actually provided. Actually not provided in this embodiment of the inverter 1 is a shunt 8 for the current flowing from the center point 5 of the half-bridge 2 to the grounding point 15 when the grounding switch 14 is closed and the switching elements 3 and 4 are actuated. Instead, a voltage between a point 24 on the connection between the center point 5 and the grounding point 15 and one of the terminals of the DC link voltage, in this case the negative terminal, is measured in this case using a measuring device 23. In this case, the point 24 is positioned between the protective resistor 13 and the grounding point 15, to be more precise in this case between the protective resistor 13 and the grounding switch 14, which in this case is arranged between the protective resistor 13 and the grounding point 15. When the voltage between the center point 5 and the same terminal of the DC link voltage to which the measuring device 23 is connected is known, i.e. the driving voltage of the current flowing via the connection to the grounding point 15 with respect to this terminal of the DC link voltage, the voltage drop across the protective resistor 13 can be determined in accordance with Kirchhoff's voltage law and from this the current flowing through the protective resistor 13 to the grounding point 15 can be calculated. An additional shunt 8 is not required here.

In the case of the inverter 1 shown in FIG. 3, in the same way as in the case of the inverter 1 shown in FIG. 2, not only an AC voltage driving an alternating current via the connection to the grounding point 15 that covers the entire range of the DC link voltage, i.e. its negative maximum corresponds to the voltage of the negative terminal of the DC link voltage with respect to ground and its positive maximum corresponds to the voltage of the positive terminal of the DC link voltage with respect to ground, can be set at the filter output 25. Rather, it is also possible for other driving voltages with respect to ground to be set within these limits at the filter output 25, to be precise both AC voltages and DC voltages, i.e. voltages that are kept constant over relatively long periods of time. Both are possible by virtue of clocking of the switching elements 3 and 4, for example, in accordance with the principles of pulse width modulation, wherein, owing to different pulse widths, different voltages between the voltages of the two terminals of the DC link voltage with respect to ground are set at the filter output 25. AC voltages set in this way at the filter output 25 can also be those that do not change their polarity with respect to ground, with the result that the current flowing via the connection to the grounding point 15 does not change its direction of current flow either.

When the grounding switch 14 is open, the measuring device 23 can be used to measure the voltage at the output of the inverter 1 downstream of a line filter of the inverter 1, consisting of the line choke 10 and the filter capacitor 19.

In the left-hand part of FIG. 3, the component parts associated with the actual circuit of the inverter 1 are enclosed by a dotted line 26. The filter capacitor 19 is also arranged therein. Whether the filter capacitor 19 is actually provided and contact is made therewith as illustrated is dependent on the topology of the respective inverter 1, however.

Figure 4:
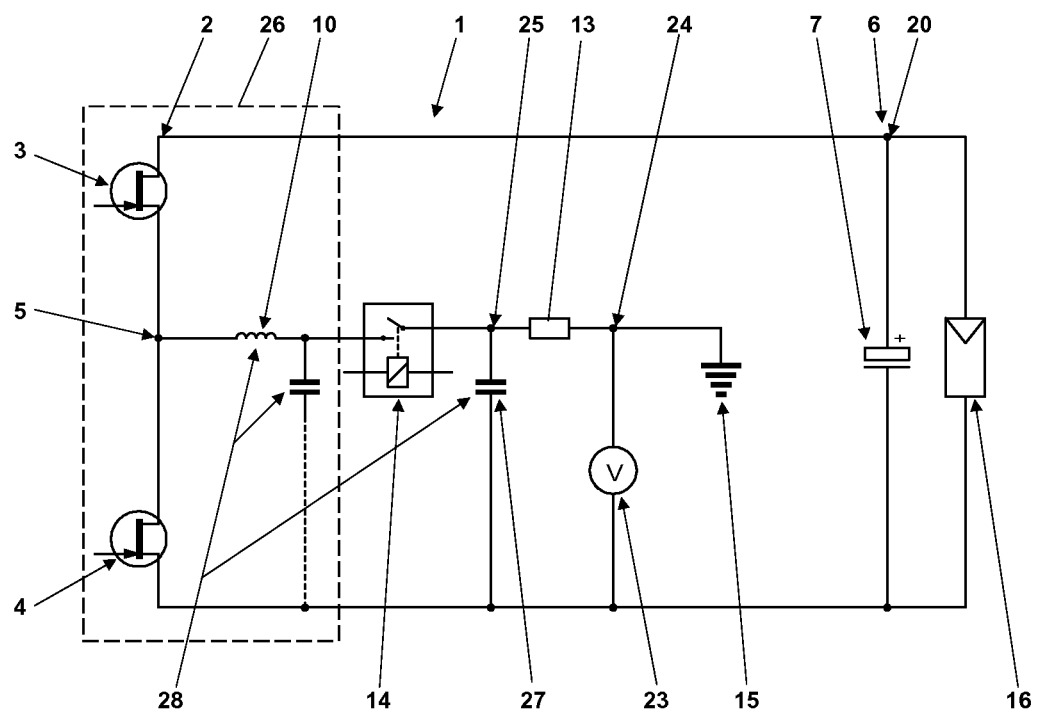
FIG. 4 illustrates the essential component parts of a further embodiment of an inverter according to the present disclosure comprising an apparatus for measuring an insulation resistance.

FIG. 4 shows, in an illustration corresponding to that in FIG. 3, yet a further embodiment of an inverter according to the present disclosure. This embodiment has the following differences over the embodiment shown in FIG. 3: the grounding switch 14 is arranged between the line choke 10 and the protective resistor 13 to be precise between a filter capacitor 19 which, depending on the present inverter topology, is connected to the negative terminal of the DC link voltage in the region of the inverter 1, wherein its optional connection is indicated by a dashed line, and an additional filter capacitor 27 that is connected to the filter output 25. When the grounding switch 14 is open, this additional filter capacitor 27 is isolated from the inverter and does not influence its behavior in any way. When the grounding switch is closed, the filter capacitor 27, in the sense of a smoothing capacitance, eliminates higher-frequency fluctuations in the driving voltage at the center point 5, which occur at the switching frequency of the switching elements 3. The filter 28, at whose filter output 25 the voltage driving the current to the grounding point is present, in this case also includes the filter capacitor 27, therefore. Owing to the filter capacitor 27, the component parts arranged outside the dotted line 26, i.e. outside the actual inverter topology, can be designed independently of the actual topology of the inverter 1. However, the measuring device 23 positioned downstream of the grounding switch 14 in this case can only be used when the grounding switch 23 is closed and therefore cannot be used for measuring the voltage at the output of the bridge of the inverter 1.

There is no functional difference between the embodiments of the inverter 1 shown in FIGS. 3 and 4 that goes beyond this.

Many variations and modifications may be made to the preferred embodiments of this disclosure without departing substantially from the spirit and principles of this disclosure. All such modifications and variations are intended to be included herein within the scope of the present disclosure, as defined by the following claims.

The invention claimed is:

1. A method of measuring an insulation resistance for an inverter having at least one half-bridge comprising two series-connected active switching elements for driving an output current, and a DC link voltage circuit, the method comprising:
connecting a center point of the half-bridge of the inverter positioned between the two series-connected active switching elements to a grounding point by closing a grounding switch, and connecting the center point connected to the grounding point, one after the other, to a first ungrounded terminal by means of a first active switching element of the two series-connected active switching elements and a second ungrounded terminal of the DC link voltage circuit of the inverter by means of a second active switching element of the two series-connected active switching elements of the half-bridge to establish first and second connections between the first and second ungrounded terminals of the DC link voltage circuit, respectively, and the grounding point; and
measuring a current flowing via the first and second connections to the grounding point using a measuring device.

2. The method of claim 1, wherein, when measuring the current flowing via the connection to the grounding point, the center point of the half-bridge is disconnected from an AC grid that is connected to the center point during a normal operation of the inverter.

3. The method of claim 1, wherein measuring the current flowing via the connection to the grounding point comprises measuring a voltage drop across a shunt that is connected between the center point of the half-bridge and the grounding point.

4. The method of claim 3, wherein the voltage drop across the shunt is measured by a measuring device of the inverter during an insulation resistance measurement operation of the inverter, and wherein the measuring device measures a voltage drop across a different shunt with a lower resistance than the shunt during a normal operation of the inverter in order to measure a current flowing from the half-bridge into the connected AC grid during the normal operation of the inverter.

5. The method of claim 1, wherein the connecting comprises closing the first and second active switching elements one after the other in order to allow two direct currents to flow one after the other from the first and second ungrounded terminals of the DC link voltage circuit, respectively, via the connection to the grounding point.

6. The method of claim 1, wherein the connecting comprises actuating the first and second active switching elements in order to allow an alternating current to flow through a line choke of the inverter via the connection to the grounding point, wherein in an insulation resistance measurement operation of the inverter the alternating current has a period that is longer than an alternating current output by the line choke during a normal operation of the inverter by at least a factor of 2.

7. The method of claim 1, wherein the connecting comprises actuating the two series-connected switching elements in order to set at least one driving voltage for the current flowing through a line choke of the inverter that is connected to the grounding point that is between the voltages of the first and second ungrounded terminals of the DC link voltage circuit with respect to ground, the at least one driving voltage provided at a filter output of a filter connected downstream of the center point of the half-bridge.

8. The method of claim 1, further comprising measuring a voltage driving the respective current via the connection to the grounding point using an additional measuring device.

9. The method of claim 6, wherein, in order to measure the current flowing via the connection to the grounding point, a voltage that is present between a point positioned between a protective resistor and the grounding point and one of the ungrounded terminals of the DC link voltage circuit is determined.

10. An inverter, comprising:
a first ungrounded terminal and a second ungrounded terminal, between which a DC link voltage circuit is present;
a half-bridge of the inverter connected between the first and second ungrounded terminals, wherein the half-bridge of the inverter comprises two series-connected active switching elements for driving an output current and a center point positioned between the two series-connected active switching elements; and
an apparatus for measuring an insulation resistance of an input source associated with the inverter, wherein the apparatus comprises a grounding switch configured to connect the center point of the half-bridge of the inverter to a grounding point, and wherein the apparatus is configured to connect the center point connected to the grounding point, one after the other, to the first and second ungrounded terminals by means of a first active switching element and a second active switching element of the two series-connected active switching elements of the half-bridge, respectively, to establish first and second connections between the first and second ungrounded terminals and the grounding point, respectively, and wherein the apparatus is configured to measure a current flowing via the first and second connections to the grounding point using a measuring device.

11. The inverter of claim 10, wherein the apparatus is configured to open a mains switch of the inverter in order to disconnect the center point of the half-bridge from an AC grid that is connected during a normal operation of the inverter in order to measure the current flowing via the connection to the grounding point.

12. The inverter of claim 11, wherein the apparatus further comprises a shunt arranged in the connection from the center point of the half-bridge to the grounding point, and wherein the apparatus is configured to measure the current flowing via the connection to the grounding point as a voltage drop across the shunt.

13. The inverter of claim 12, wherein the shunt is connected in series with the grounding switch and a protective resistor.

14. The inverter of claim 12, wherein the apparatus is configured to measure the voltage drop across the shunt using a measuring device of the inverter during an insulation resistance measurement operation of the inverter, and wherein the measuring device is configured to measure a voltage drop across a different shunt having a lower resistance than the shunt during a normal operation of the inverter in order to measure a current from the half-bridge into the connected AC grid during the normal operation of the inverter.

15. The inverter of claim 14, wherein the connection to the grounding point of the apparatus branches off, downstream of the half-bridge, from a current path via which the center point of the half-bridge is connected to the AC grid during a normal operation of the inverter, wherein the measuring device is connected across the shunt and the different shunt with the lower resistance.

16. The inverter of claim 15, wherein the apparatus further comprises a changeover switch that conducts the current from the center point of the half-bridge either through the shunt or the different shunt with the lower resistance, and wherein the measuring device is connected to a branch to the shunts and is connected to a connection terminal of the changeover switch that is on the other side thereof.

17. The inverter of claim 10, wherein the apparatus is configured to close the first and second active switching elements one after the other in order to allow two direct currents to flow, one after the other, from the first and second ungrounded terminals, respectively, via the connection to the grounding point.

18. The inverter of claim 10, wherein the apparatus is configured to actuate the two series-connected active switching elements in order to allow an alternating current to flow via the connection through a line choke of the inverter to the grounding point, wherein in an insulation resistance measurement operation of the inverter the alternating current has a longer period than that of an alternating current output by the line choke during a normal operation of the inverter by at least a factor of 2.

19. The inverter of claim 10, wherein the apparatus is configured to actuate the two series-connected active switching elements in order to set at least one driving voltage for the current flowing through a line choke of the inverter that is connected to the grounding point that is between the voltages of the first and second ungrounded terminals with respect to ground at a filter output of a filter connected downstream of the center point of the half-bridge.

20. The inverter of claim 10, wherein the apparatus further comprises an additional measuring device configured to measure a voltage driving the respective current flowing via the connection to the grounding point.

21. The inverter of claim 18, further comprising a filter capacitor connected in parallel with the shunt.

22. The inverter of claim 18, wherein the measuring device for measuring the current flowing via the connection to the grounding point is configured to measure a voltage that is present between a point positioned between a protective resistor and the grounding point and one of the first and second ungrounded terminals.

23. The inverter of claim 22, wherein the point is positioned between the protective resistor and the grounding switch.

24. The inverter of claim 22, wherein the protective resistor is positioned between the grounding switch and the grounding point.

25. The inverter of claim 22, further comprising a filter capacitor connected between the connection to the grounding point and one of the first and second ungrounded terminals at a filter output between a line choke of the inverter and the protective resistor.

* * * * *